United States Patent
Wolff et al.

(10) Patent No.: US 11,071,820 B2
(45) Date of Patent: Jul. 27, 2021

(54) INFUSION DEVICE CONSTITUTED TO DETECT AN ABNORMAL CONDITION DURING BOLUS INJECTION

(71) Applicant: Fresenius Vial SAS, Brézins (FR)

(72) Inventors: Rémy Wolff, Morette (FR); Christine Durand, Chassieu (FR)

(73) Assignee: Fresenius Vial SAS, Brézins (FR)

( * ) Notice: Subject to any disclaimer, the term of this patent is extended or adjusted under 35 U.S.C. 154(b) by 133 days.

(21) Appl. No.: 16/461,365

(22) PCT Filed: Nov. 17, 2017

(86) PCT No.: PCT/EP2017/079560
§ 371 (c)(1),
(2) Date: May 15, 2019

(87) PCT Pub. No.: WO2018/104027
PCT Pub. Date: Jun. 14, 2018

(65) Prior Publication Data
US 2019/0307956 A1     Oct. 10, 2019

(30) Foreign Application Priority Data

Dec. 9, 2016 (EP) .................................... 16306651

(51) Int. Cl.
*A61M 5/168* (2006.01)
*A61M 5/145* (2006.01)

(52) U.S. Cl.
CPC ........ *A61M 5/16854* (2013.01); *A61M 5/145* (2013.01); *A61M 5/1456* (2013.01);
(Continued)

(58) Field of Classification Search
CPC ............ A61M 5/16854; A61M 5/1456; A61M 2005/16868; A61M 2205/18;
(Continued)

(56) References Cited

U.S. PATENT DOCUMENTS 6,423,035 B1*   7/2002   Das ..................... A61M 5/1456
                                                    128/DIG. 1
2002/0107476 A1*   8/2002   Mann .................. A61M 5/1723
                                                    604/67
(Continued)

FOREIGN PATENT DOCUMENTS

JP     2001-245978 A    9/2001
WO  WO 2014/105606 A1   7/2014
(Continued)

OTHER PUBLICATIONS

International Search Report and Written Opinion, counterpart International Appl. No. PCT/EP2017/079560 (dated Jan. 17, 2018) (21 pages).

*Primary Examiner* — Bhisma Mehta
*Assistant Examiner* — Neeraja Gollamudi
(74) *Attorney, Agent, or Firm* — Cook Alex Ltd.

(57) ABSTRACT

Infusion device constituted to detect an abnormal condition during bolus injection An infusion device (1) for administering a medical fluid to a patient (4) comprises a pumping mechanism (12) for pumping a medical fluid through an infusion line (3) towards a patient (4), a sensor device (120) for measuring a measurement value indicative of a pressure in the infusion line (3), and a control device (13) being constituted to control the pumping mechanism (12) for injecting a bolus of medical fluid into the infusion line (3). Herein, the control device (13) is constituted to determine, dependent on an injection of a bolus into the infusion line (3), a control parameter taking a change in pressure during injection of the bolus into account and to derive, from the control parameter, the presence of an abnormal condition during the injection of the bolus. In this way an infusion device is provided which in a reliable manner allows for the (Continued)

detection of an abnormal condition during the administration of a bolus.

20 Claims, 1 Drawing Sheet

(52) U.S. Cl.
CPC ............ *A61M 2005/16868* (2013.01); *A61M 2205/18* (2013.01); *A61M 2205/332* (2013.01); *A61M 2205/3334* (2013.01); *A61M 2205/3355* (2013.01)

(58) Field of Classification Search
CPC .... A61M 2205/332; A61M 2205/3334; A61M 2205/3355; A61M 2005/16863; A61M 2205/333; A61M 2205/04
See application file for complete search history.

(56) References Cited

U.S. PATENT DOCUMENTS

| | | | |
|---|---|---|---|
| 2005/0096593 A1* | 5/2005 | Pope | A61M 5/1452 604/122 |
| 2007/0191770 A1* | 8/2007 | Moberg | A61M 5/1452 604/131 |
| 2012/0215199 A1 | 8/2012 | Moberg et al. | |
| 2014/0121632 A1* | 5/2014 | Haenggi | A61M 5/1456 604/500 |
| 2015/0005732 A1 | 1/2015 | Halbert et al. | |
| 2016/0331895 A1 | 11/2016 | Pope et al. | |

FOREIGN PATENT DOCUMENTS

| WO | WO 2016/030836 A1 | 3/2016 |
|---|---|---|
| WO | WO 2016/168162 A1 | 10/2016 |

\* cited by examiner

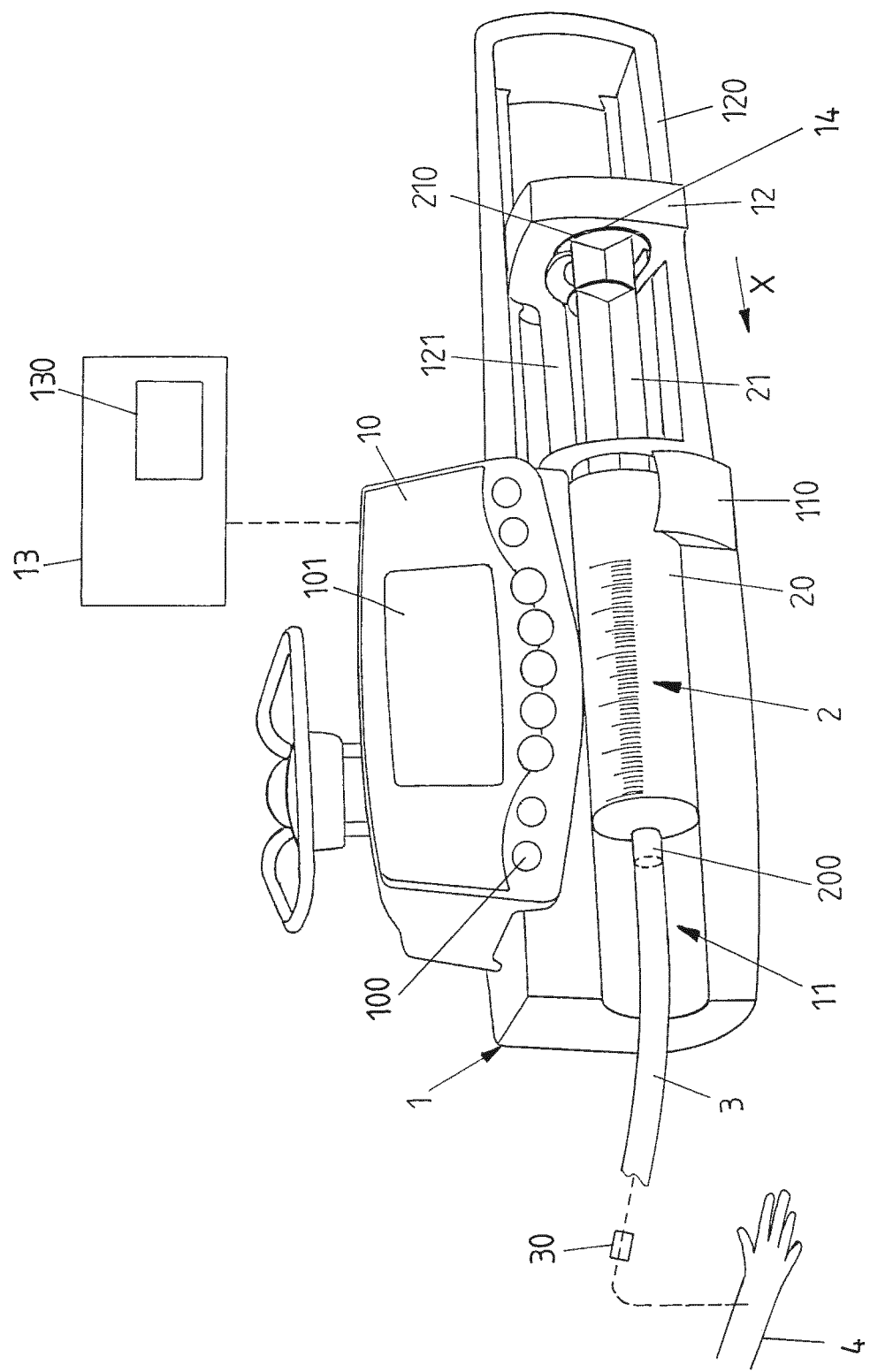

INFUSION DEVICE CONSTITUTED TO DETECT AN ABNORMAL CONDITION DURING BOLUS INJECTION

The present application is a U.S. National Stage of PCT International Patent Application No. PCT/EP2017/079560, filed Nov. 17, 2017, which claims priority to EP Application No. 16306651, filed Dec. 9, 2016, both of which are hereby incorporated herein by reference.

The invention relates to an infusion device for administering a medical fluid to a patient according to the preamble of claim 1 and to a method for operating an infusion device.

An infusion device of this kind comprises a pumping mechanism for pumping a medical fluid through an infusion line towards a patient. A sensor device, in particular a force sensor, serves for measuring a measurement value indicative of a pressure in the infusion line, and a control device is constituted to control the pumping mechanism for injecting a bolus of medical fluid into the infusion line.

It is to be noted that an infusion device of this kind may be constituted for example by a syringe pump comprising a syringe to which the infusion line is connected and onto which a pumping mechanism in the shape of a pusher device acts in order to deliver a medical fluid from the syringe through the infusion line towards a patient. The infusion device however may also be constituted as a volumetric (peristaltic) infusion pump comprising a pumping mechanism, for example comprising a wobbling mechanism, acting onto the infusion line in order to pump medical fluid through the infusion line towards a patient.

Medication in a fluid state can be infused into a patient using an infusion line. The infusion line is connected to a fluid source such as, in case of a syringe pump, a syringe that stores the medication. The medication can in this case be pushed out of the syringe through the infusion line towards the patient using a pusher device acting onto the syringe for continuously pushing a piston into a cylindrical tube in order to deliver medication from the cylindrical tube of the syringe via the infusion line towards the patient.

During such an infusion process an occlusion may occur in the infusion line, which, in some cases, may be hazardous for the patient. There hence is a need to reliably detect an occlusion occurring in an infusion line in order to avoid injuries resulting from occluded infusion lines.

From the state of the art methods for detecting an occlusion in an infusion line during an infusion process are known that are based on the assumption that an occlusion causes a rise of the pressure in the infusion line. An increase in pressure causes, in case of a syringe pump, the force applied to the syringe by a means of pumping device for pushing the medication through the infusion line towards the patient to increase. By monitoring the force applied to the syringe, hence, the actual pressure in the infusion line can be deduced and accordingly, if the actual pressure exceeds a threshold value, an alarm signal indicative of an occlusion can be triggered. In case of a volumetric (peristaltic) infusion device a force sensor may be placed directly on the infusion line in order to measure the pressure within the infusion line.

During an infusion process medical fluid is continuously pumped through the infusion line towards the patient, for example at a constant, set dose rate. During the infusion process the pressure in the infusion line is constantly observed by means of the sensor device in order to potentially detect an occlusion present on the infusion line, which may hinder delivery of medical fluid towards the patient.

During an ongoing infusion process or even when no infusion is performed a (additional) bolus may be injected towards the patient in order to effect the delivery of additional medical fluid towards the patient. A bolus generally is defined as the administration of a discrete amount of medical fluid, such as a medication, a drug or another compound, towards a patient in order to raise its concentration in the patient's blood to an effective level.

During an ongoing infusion operation, for the detection of a potential occlusion the injection of one or multiple boluses is taken into account in that each injection of a bolus will contribute to the rise in pressure in the infusion line in case of an occlusion such that generally no particular treatment of boluses is required. In case no infusion is ongoing, however, the case may occur that a repeated administration of multiple boluses may not trigger an occlusion alarm because a detection threshold may not be exceeded by the repeated boluses. If an occlusion subsequently is released however and the medical fluid associated with the repeated boluses at once is delivered to the patient, a hazardous condition for the patient may occur.

For example, in a hospital environment it is conceivable that a nurse leaves a stopcock on an infusion line closed overnight. If a patient nevertheless requests a repeated administration of boluses, the sum of all boluses may not be sufficient to reach a pressure threshold associated with an occlusion detection such that no alarm is raised. If a nurse in the morning detects that the stopcock has been closed and opens the stopcock, the sum of all boluses requested by the patient overnight may be administered to the patient at once, potentially creating a hazard for the patient.

There hence is a desire to be able to detect an abnormal condition during the administration of a bolus, such as for example due to a closed stopcock on the infusion line. It herein must be taken into account that usually, during the administration of a bolus, false alarms should be avoided, since naturally the administration of a bolus will lead to an increase in pressure in the infusion line due to the additional volume of fluid present in the infusion line. For this, during a regular infusion process typically an occlusion detection threshold is set to a high value, for example, in order to avoid an occlusion detection during the injection of a bolus.

It is an object of the invention to provide an infusion device and a method for operating an infusion device which in a reliable manner allow for the detection of an abnormal condition during the administration of a bolus.

This object is achieved by means of an infusion device comprising the features of claim 1.

Accordingly, the control device is constituted to determine, dependent on an injection of a bolus into the infusion line, a control parameter taking a change in pressure during injection of the bolus into account and to derive, from the control parameter, the presence of an abnormal condition during the injection of the bolus.

Hence, the infusion device is constituted to monitor a change in pressure during the administration of a bolus. If it is found that, during the administration of the bolus, an abnormal rise in pressure occurs, it is concluded that an abnormal condition is present causing this rise in pressure. The control parameter, for this, is determined specifically during the administration of the bolus, such that it is observed how the pressure in the infusion line behaves during the injection of the bolus in order to draw conclusions with regard to a potential abnormal condition.

The bolus may for example be requested by a user, for example the patient himself, by inputting a specific command into the infusion device, for example by pressing a dedicated button on the infusion device. Upon requesting the injection of the bolus, the control device controls the pumping mechanism such that a bolus having a predefined, discrete volume is injected into the infusion line towards the patient.

During the injection of the bolus it is observed whether the pressure in the infusion line abnormally rises. This takes place by computing the control parameter, which for example takes into account a change in pressure in between a first time at the start or prior to the injection of the bolus and a second time at the end of or after the injection of the bolus. For this, the sensor device measures a measurement value indicative of the pressure in the infusion line at the first time and a measurement value indicative of the pressure in the infusion line at the second time. By forming the difference between the two pressure values it can be detected by which amount the pressure has risen during the injection of the bolus.

In one embodiment, the control device is constituted to determine the control parameter according to an equation taking the difference in pressure between the first time and the second time, a volume of the injected bolus, and an expected slope during a pressure rise in case of an occluded infusion line into account, for example according to the following equation:

$$C = \frac{P(t_2)[\text{bar}] - P(t_1)[\text{bar}]}{V_{Bolus}[\text{ml}] \cdot \text{Expected\_Slope}[\text{bar}/\text{ml}]}$$

Herein, C is the control parameter, $P(t_1)$ is the pressure in the infusion line (3) at the first time and $P(t_2)$ is the pressure in the infusion line (3) at the second time, $V_{Bolus}$ is the volume of the injected bolus, and Expected_Slope corresponds to an expected slope during a pressure rise in case of an occluded infusion line.

In this equation, the quotient of the pressure difference and the discrete volume of the injected bolus corresponds to the actual slope. This is divided by the slope of the pressure rise that can be expected, taking system parameters into account, when an occlusion is present on the infusion line. If the control parameter assumes the value 1, the actual slope equals the expected slope. If the control parameter is close to 1, the actual slope at least is in the vicinity of the expected slope. This may indicate that an occlusion is present in the infusion line during injection of the bolus, for example due to a closed stopcock on the infusion line.

The detection of the abnormal condition hence is based on a comparison of the actual slope to an expected slope (that can be expected during the presence of an occlusion) for a pressure rise during injection of a bolus. If it is found that the actual slope is at least close to the expected slope, it is assumed that an abnormal condition equal or similar to the presence of an occlusion, for example due to a closed stopcock, is present on the infusion line.

This is based on the finding that for a particular system using a particular syringe in connection with a particular infusion line the pressure inside the line will, in case of an occlusion, rise at a specific slope determined by the characteristics of the infusion line and the syringe. Hence, by observing the slope it can be determined whether the slope of the pressure within the infusion line is close to the slope that is expected in case of an occlusion or not. Hence, by monitoring whether the slope of the pressure within the infusion line falls into a range around the expected slope, it in principle can be detected whether an occlusion (or a similar abnormal condition) is present or not, even independent of a comparison of the absolute pressure value with a threshold.

The expected slope can be computed taking characteristics of the system into account. Characteristics can be stored for example in a storage device such as a database of the infusion device, such that the expected slope can be computed prior to the start of an infusion process when, in case of a syringe pump, a particular syringe in connection with a particular infusion line to be used for an infusion process is identified to the system by a user, for example a nurse.

The expected slope, in case of a syringe pump, is for example influenced by the compliance of the syringe, the compliance of the infusion line, a stiffness of the pusher device and/or a dimension of the cylindrical tube. The compliance herein indicates a measure for the expansibility of the system, for example the expansibility of the cylindrical tube of the syringe used on the infusion device or the expansibility of the infusion line connected to the cylindrical tube. Generally, the compliance indicates the change of volume for a change in pressure and accordingly is stated for example in ml/bar. With respect to for example the infusion line, the compliance indicates by what volume the infusion line expands if the pressure increases by a certain margin.

The compliance of a syringe, for example, is dependent on different physical characteristics of the syringe. Among such characteristics are for example the elasticity of the cylindrical housing and the rubber stopper elasticity, the rubber stopper elasticity likely having a stronger influence on the syringe compliance. For determining the compliance for a particular syringe, a calibration measurement can be performed in which all characteristics of the syringe that could influence it (cylindrical housing, stopper, piston stiffness etc.) are naturally taken into account.

For different syringes and different infusion lines, different characteristic values, for example compliance values, can be stored in the system, such that a particular set of values is chosen to compute the expected slope if a particular syringe in connection with a particular infusion line is to be used for an infusion process.

In case of an infusion device in the shape of a volumetric (peristaltic) infusion pump the expected slope may be estimated from the compliance of the infusion line alone.

It may be concluded that an abnormal condition during the injection of the bolus is present if the control parameter is larger than a first bound and/or is smaller than a second bound greater than the first bound. The first bound may for example be 0.5. The second bound may for example be 1.5. As said, if the control parameter has the value 1, the actual slope equals the expected slope. If it is found that the control parameter lies in a range around the value 1, it may be concluded that something hinders the flow through the infusion line, such that it may be concluded for an abnormal condition.

In one embodiment, the infusion device comprises an output device for outputting an alarm message, for example a display device for outputting visual messages such as written text or the like or an acoustic output device for outputting acoustic signals. The control device may trigger the output of an alarm message in case it is concluded that an abnormal condition during the injection of a bolus is present. Hence, if it is found that the control parameter lies within a predefined range indicating the presence of an abnormal condition, an alarm message may be triggered for example by outputting a text message via a display device of the infusion device.

In one embodiment, a stopcock may be placed on the infusion line. In this case, the abnormal condition may correspond to a closed stopcock hindering flow of medical fluid through the infusion line.

In principle, the infusion device may be constituted as any sort of pumping device suitable to pump medical fluid through an infusion line towards a patient. In one embodiment, the infusion device is a syringe pump. In another embodiment, the infusion device is a volumetric (peristaltic) infusion pump.

The object is also achieved by means of a method of operating an infusion device for administering a medical fluid to a patient, wherein in the method: a control device controls a pumping mechanism for injecting a bolus of medical fluid into an infusion line, and a sensor device measures a measurement value indicative of a pressure in the infusion line. Herein, the control device determines, dependent on an injection of a bolus into the infusion line, a control parameter taking a change in pressure during injection of the bolus into account and derives, from the control parameter, the presence of an abnormal condition during the injection of the bolus.

The advantages and advantageous embodiments described above for the infusion device equally apply also to the method such that it shall be referred to the above.

The idea underlying the invention shall subsequently be described in more detail with respect to the embodiments shown in the FIGURES. Herein:

FIG. 1 shows a view of an embodiment of an infusion device in the shape of a syringe pump.

FIG. 1 shows an embodiment of an infusion device 1 in the shape of a syringe pump having a housing 10 and a receptacle 11 arranged on the housing 10 to receive a syringe 2 therein.

The syringe 2 comprises a cylindrical tube 20 which, when installing the syringe 2 on the infusion device 1, contains a medical liquid, for example a medication, to be infused to a patient 4. The cylindrical tube 20 is connected, via a connector 200, to an infusion line 3 which may extend from the syringe 2 towards a patient 4 for infusing the medical liquid to the patient 4.

For installing the syringe 2 on the receptacle 11 of the infusion device 1, the cylindrical tube 20 of the syringe 2 is placed in the receptacle 11 and is mechanically connected to the housing 10 by means of a fixation device 110. By means of the fixation device 110, for example constituted by a releasable clamp element, the cylindrical tube 20 is secured within the receptacle 11 such that the cylindrical tube 20 is held in position on the receptacle 11.

The syringe 2 comprises a piston 21 which, for delivering medical fluid contained in the cylindrical tube 20, can be pushed into the cylindrical tube 20 in a pushing direction X. For this, the infusion device 1 comprises a pumping mechanism in the shape of a pusher device 12 movably arranged within a guide device 120 and connected to a suitable drive mechanism via a connecting rod 121.

For operating the infusion device 1, the syringe 2 is installed on the infusion device 1 and, for performing an infusion process, the pusher device 12 is electrically moved, controlled by a control device 13 of the infusion device 1, in the pushing direction X to move the piston 21 into the cylindrical tube 20 for delivering the medical fluid contained in the cylindrical tube 20 via the infusion line 3 towards the patient 4.

Generally, if during an infusion process an occlusion occurs on the infusion line 3 connected to the cylindrical tube 20 of the syringe 2, the pressure in the infusion line will rise. To detect an occlusion, hence, the pressure in the infusion line 3 can be observed, and when an abnormal rise in pressure is found it can be concluded that an occlusion is present.

To observe the pressure in the infusion line 3, the force applied to the piston head 210 of the piston 21 by means of the pusher device 12 is measured by a sensor device 14 in the shape of a force sensor placed on the pusher device 12 facing the piston head 210. The force measured in this way allows for an indirect measurement of the pressure within the cylindrical tube 20, which generally equals the pressure in the infusion line 3.

In particular, the pressure in the cylindrical tube 20 depends on the measured force according to the following relation:

$$P = \frac{F - F_0}{S}.$$

Herein, P denotes the pressure, F denotes the measured force, $F_0$ denotes a frictional force component and S denotes the effective surface by which the piston 21 acts onto the liquid contained in the cylindrical tube 20. The effective surface S is substantially determined by the inner diameter of the cylindrical tube 20. Whereas F is measured and S is known from the geometrical dimensions of the cylindrical tube 20 of the syringe 2, the frictional force component $F_0$ may vary in dependence on the specific syringe 2 used on the system and may additionally depend on the position of the piston 21 within the cylindrical tube 20 and on the velocity by which the piston 21 is moved relative to the cylindrical tube 20 during an infusion process. For the frictional force component $F_0$ for example a constant may be assumed, or a mathematical model may be used to determine the frictional force component $F_0$ for a particular syringe 2.

By determining the pressure P in this way and for example by comparing the determined pressure P to a predefined threshold it can be concluded whether an occlusion is present in the infusion line 3 or not. If it for example is found that the pressure P rises above the threshold, it is concluded that an occlusion is present.

An occlusion or another flow interruption (due for example to a closed stopcock 30 placed on the infusion line 3) in a particular system will generally cause a rise of the measured force according to a rather well-defined slope, which can be determined when mechanical characteristics of the system such as the compliance of the infusion line 3, the compliance of the syringe 2 and the stiffness of the mechanical system of the pusher device 12 are known.

The expected slope is the theoretical slope that the pressure should follow in case the line is occluded at the catheter level. It depends on:
  the flowrate,
  the syringe mechanical properties (especially the syringe stopper stiffness),
  the syringe pump mechanical properties (especially the pusher stiffness),
  the infusion line mechanical properties (the tube compliance).
  the fluid properties (which can be neglected if it is assumed that the fluid to be pumped is an incompressible liquid).

The pressure slope can either be expressed referring to time or referring to volume. Expressing the expected slope with reference to volume, the expected slope at a position i during movement of the piston 21 of the comes out to be:

$$\text{Expected\_slope}(i)[\text{bar}/\text{ml}] = \frac{dP(i)[\text{bar}]}{d\text{Volume}(i)[\text{ml}]}$$

The expected slope is equivalent to a volumetric stiffness, which is the inverse of the system compliance. One can therefore write $$\frac{1}{\text{Volumetric\_Stiffness}[\text{bar}/\text{ml}]} = \sum_{k=1}^{3} \frac{1}{\text{Volumetric\_Stiffness}(k)[\text{bar}/\text{ml}]}$$

Where $$\begin{cases} \text{Volumetric\_Stiffness}(1)[\text{bar}/\text{ml}] = \frac{1}{\text{Syringe\_Compliance}[\text{ml}/\text{bar}]} \\ \text{Volumetric\_Stiffness}(2)[\text{bar}/\text{ml}] = \frac{1}{\text{Line\_Compliance}[\text{ml}/\text{bar}]} \\ \text{Volumetric\_Stiffness}(3)[\text{bar}/\text{ml}] = \frac{100 \cdot \text{Pusher\_Stiffness}[\text{gf}/\text{mm}]}{\text{Syringe\_Surface}[\text{mm}^2]^2} \end{cases}$$

and the expected slope comes out to be:

$$\text{Expected\_slope}[\text{bar}/\text{ml}] = \frac{1}{\text{Syringe\_Compliance}[\text{ml}/\text{bar}] + \text{Line\_Complince}[\text{ml}/\text{bar}] + \frac{\text{Syringe\_Surface}[\text{mm}^2]^2}{100 \cdot \text{Pusher\_Stiffness}[\text{gf}/\text{mm}]}}$$

This can be converted to a slope by millimeter, assuming that for a different syringe 1 mm is equivalent to (syringe_Surface S [mm²]/1000) ml:

$$\text{Expected\_slope}[\text{bar}/\text{mm}] = \frac{\text{Synringe\_Surface}[\text{mm}^2]}{1000 \cdot (\text{Syringe\_Compliance}[\text{ml}/\text{bar}] + \text{Line\_Compliance}[\text{ml}/\text{bar}]) + 10 \cdot \frac{\text{Syringe\_Surface}[\text{mm}^2]^2}{\text{Pusher\_Stiffness}[\text{gf}/\text{mm}]}}$$

This also can be converted to gf/mm. Assuming that for a given syringe F [gf]=10.2*P [bar]*S [mm²], the slope in bar/mm can be converted into a slope in gf/mm:

$$\text{Expected\_slope}[\text{gf}/\text{mm}] = \frac{0.0102 \cdot \text{Syringe\_Surface}[\text{mm}^2]^2}{(\text{Syringe\_Compliance}[\text{ml}/\text{bar}] + \text{Line\_Compliance}[\text{ml}/\text{bar}]) + \frac{\text{Syringe\_Surface}[\text{mm}^2]^2}{\text{Pusher\_Stiffness}[\text{gf}/\text{mm}]}}$$

Example parameter values for a 5 cc syringe of a particular brand and a particular infusion device are summarized in Table 3:

TABLE 3

| Parameter | Value |
| --- | --- |
| Syringe_Compliance | 0.0566 ml/bar |
| Line_Compliance | 0.145 ml/bar |
| Pusher_Stiffness | 9279 gf/mm |
| Syringe inner diameter | 11.87 mm |
| Syringe surface S | 110.66 mm² |

Using these parameters, the following values for the expected slope are obtained:
Expected_Slope [bar/ml]=4.65 [bar/ml]
Expected_Slope [bar/mm]=0.514 [bar/mm]
Expected_Slope [gf/mm]=568.8 [gf/mm]
This expected slope is independent of the flow rate.

Thus, it can be assumed that, in the above case, the expected slope in case of an occlusion will be close to 0.5 bar/mm for the particular syringe and the particular infusion device for which the parameters are valid.

The expected slope may for example be computed for the particular parameters of the infusion line 3, the syringe 2 and the device 1 in use upon installation of a particular syringe 2 in connection with an infusion line 3 on the infusion device 1. In test measurements it was found that the expected slope in case of an occlusion is well distinguished from any slope that usually arises during a normal infusion process when no occlusion is present.

In order to allow the computation of the expected slope, the infusion device 1 comprises a storage device 130, for example in the shape of a database, in which relevant parameters of different syringes 2 and infusion lines 3 which potentially may be used on the infusion device 1 are stored. In the storage device 130 in particular a syringe compliance for one or multiple syringes 2, a line compliance for one or multiple infusion lines 3, a pusher stiffness of the pusher device 12 (including its driving mechanism), and geometric data of one or multiple syringes 2, in particular an inner diameter of the cylindrical tube 20, may be stored. Hence, upon identification of a particular syringe 2 and a particular infusion line 3 by a user, for example by inputting suitable control data into the infusion device 1 upon installation of the syringe 2 and the infusion line 3 on the infusion device 1, the expected slope can be computed and can be used as it shall be described subsequently.

Knowing the expected slope, generally an occlusion can be detected by comparing the actual slope of a pressure rise in the infusion line 3 to the expected slope. In addition and independent of the occlusion detection during an infusion process using the expected slope it can be detected whether during the injection of a bolus an abnormal condition, in particular an occlusion in the infusion line 3 or a closed stopcock 30, exist.

Boluses may be injected into the infusion line 3 independent of an ongoing infusion operation. The injection of boluses may for example be triggered by the patient 4 himor herself, for example by pressing a suitable button 100 on the infusion device 1, causing the control device 13 to initiate injection of a bolus (i.e., the administration of a discrete amount of the medical fluid contained in the cylindrical tube 20 to the patient 4) by correspondingly moving the pusher device 12 by a predefined distance.

Herein, the following scenario may occur:

A patient 4 may, overnight, request multiple boluses by pressing the button 100 on the infusion device 1. If a nurse erroneously has left the stopcock 30 closed on the infusion line 3, the pusher device 12 may upon the repeated requests of boluses be moved, but the medical fluid may not flow from the cylindrical tube 20 through the infusion line 3 due to the closed stopcock 30. If the overall volume of the multiple boluses does not cause the pressure within the infusion line 3 to exceed the predefined occlusion threshold, no occlusion alarm may be triggered. If then a nurse in the morning detects that the stopcock 30 is closed and opens the stopcock 30, this may cause the administration of the overall volume of the repeated boluses to the patient 4 at once, which may be hazardous.

Hence, there is a desire to detect an abnormal condition during the administration of a bolus, independent of an occlusion detection during a regular infusion process.

For this, a pressure rise during the injection of a bolus is monitored. For example, the pressure at the beginning or (immediately) prior to the beginning of the injection of the bolus may be obtained by a reading of the force sensor 14 in order to determine a first pressure value, and the pressure in the infusion line 3 at the end or (immediately) after the administration of the bolus may be determined by another reading of the force sensor 14 an order to obtain a second pressure value. From the difference of the second pressure value and the first pressure value a value for the rise in pressure during the injection of the bolus is obtained. By dividing the pressure difference by the defined volume of the injected bolus, an actual slope (pressure per volume) is obtained, which may be compared to the expected slope computed as described above in order to conclude whether an abnormal condition is present during the injection of the bolus.

If it is found that the actual slope of the pressure rise is at or at least close to the expected slope, it can be concluded that likely an occlusion on the infusion line 3, for example due to a closed stopcock 30, is present, such that an alarm message or at least a warning message may be triggered and for example output as a text message via a display device 101 of the infusion device 1.

In particular, the following equation may be used to compute a control parameter:

$$C = \frac{P(t_2)[\text{bar}] - P(t_1)[\text{bar}]}{V_{Bolus}[\text{ml}] \cdot \text{Expected\_Slope}[\text{bar}/\text{ml}]}$$

Herein, C is the control parameter, $P(t_1)$ is the pressure in the infusion line 3 at a first time at the beginning or prior to the administration of the bolus and $P(t_2)$ is the pressure in the infusion line 3 at a second time at the end or after the administration of the bolus. $V_{Bolus}$ is the volume of the injected bolus, and Expected_Slope corresponds to the expected slope during a pressure rise in case of an occluded infusion line computed as described above.

If the actual slope is close to the expected slope, the control parameter will assume a value close to 1. Hence, by monitoring whether the control parameter falls into a range around 1 it can be concluded whether an abnormal condition similar to an occlusion is present during the injection of the bolus.

The lower bound for the range may for example be 0.5, whereas the upper bound of the range may for example be a 1.5. Hence, if the control parameter falls into a range bounded by 0.5 and 1.5, it is concluded that an abnormal condition similar to an occlusion is present during the injection of the bolus.

It is to be understood that the bounds given are merely examples. The bounds may be suitably adjusted. For example, the lower bound may be in a range between 0.4 and 0.9, for example at 0.8, whereas the upper bound may be in a range between 1.1 and 1.6, for example at 1.2.

If it is found that the control parameter falls into the noted range, a suitable message may be output for example via the display device 101. In this way for example a nurse may be informed that during the request of a bolus the infusion line 3 has been interrupted, for example due to a closed stopcock 30, which the nurse may then take into account in the decision whether to open the stopcock 30 or not.

The invention is not limited to the embodiments described above, but may be implemented also in an entirely different fashion.

For example, a similar procedure as described above in order to detect an abnormal condition during the injection of a bolus may also be applied on an infusion device in the shape of a volumetric (peristaltic) infusion pump.

The expected slope may be determined in a different way, for example in a calibration measurement on a particular syringe and a particular infusion line. The described procedure hence only serves as an example.

LIST OF REFERENCE NUMERALS

1 Infusion device
10 Housing
100 Input device
101 Output device (display device)
11 Receptacle
110 Fixation device
12 Pumping mechanism (pusher device)
120 Guide device
121 Connecting rod
13 Control device
130 Storage device
14 Sensor device
2 syringe
20 Cylinder tube
200 Connector
21 Piston
210 Piston head
3 Infusion line
30 Stopcock
4 Patient
X Movement direction

The invention claimed is:
1. An infusion device for administering a medical fluid to a patient, comprising:
a pumping mechanism for pumping a medical fluid through an infusion line towards a patient,
a sensor device for measuring a measurement value indicative of a pressure in the infusion line, and
a control device configured to control the pumping mechanism for injecting a bolus of the medical fluid into the infusion line,
the control device being configured to determine, dependent on an injection of the bolus into the infusion line, a control parameter taking a change in the pressure during the injection of the bolus into account and to derive, from the control parameter, a presence of an abnormal condition during the injection of the bolus, the abnormal condition being an occlusion in the infusion line,
the sensor device being configured to measure a first measurement value at a first time at a start or prior to the injection of the bolus in order to derive the pressure in the infusion line at the first time, and to measure a second measurement value at a second time at an end of or after the injection of the bolus in order to derive the pressure in the infusion line at the second time, and the control device being configured to determine the control parameter according to an equation taking a difference in the pressure between the first time and the second time, a volume of the bolus, and an expected slope during a pressure rise in case of an occluded infusion line into account, wherein a quotient of the difference in the pressure and the volume of the bolus corresponds to an actual slope.

2. The infusion device according to claim 1, further comprising an input device configured to allow a user to request the bolus, the control device configured to control the pumping mechanism for injecting the bolus of the medical fluid into the infusion line upon a user's request input via the input device.

3. The infusion device according to claim 1, wherein the control device is configured to determine the control parameter according to the equation $$C = \frac{P(t_2)[\text{bar}] - P(t_1)[\text{bar}]}{V_{Bolus}[\text{ml}] \cdot \text{Expected\_Slope}[\text{bar}/\text{ml}]}$$

wherein

C is the control parameter, $P(t_1)$ is the pressure in the infusion line at the first time and $P(t_2)$ is the pressure in the infusion line at the second time, $V_{Bolus}$ is the volume of the injected bolus, and Expected_Slope corresponds to the expected slope during a pressure rise in case of an occluded infusion line.

4. The infusion device according to claim 1, wherein the expected slope is determined taking a compliance of a syringe, a compliance of the infusion line, a stiffness of the pumping mechanism and/or a dimension of a cylindrical tube into account.

5. The infusion device according to claim 4, further comprising a storage device, wherein values for the compliance of the syringe, the compliance of the infusion line, the stiffness of the pumping mechanism and/or the dimension of the cylindrical tube are stored in the storage device of the infusion device for at least one syringe used on the infusion device.

6. The infusion device according to claim 1, wherein the control device is configured to conclude the presence of an abnormal condition during the injection of the bolus if the control parameter is larger than a first bound and/or is smaller than a second bound greater than the first bound.

7. The infusion device according to claim 6, wherein the first bound is 0.5, and/or the second bound is 1.5.

8. The infusion device according to claim 1, further comprising an output device for outputting an alarm message, wherein the control device is configured to trigger the output of an alarm message in case it is derived that an abnormal condition during the injection of the bolus is presented.

9. The infusion device according to claim 1, wherein the abnormal condition corresponds to a closed stopcock preventing flow through the infusion line.

10. The infusion device according to claim 1, wherein the infusion device is a syringe pump.

11. A method of operating an infusion device for administering a medical fluid to a patient, the method comprising:

injecting a bolus of a medical fluid into an infusion line, measuring a measurement value indicative of a pressure in the infusion line, and determining, dependent on an injection of the bolus into the infusion line, a control parameter taking a change in the pressure during the injection of the bolus into account and deriving, from the control parameter, a presence of an abnormal condition during the injection of the bolus, the abnormal condition being an occlusion in the infusion line, the step of measuring a measurement value comprising measuring a first measurement value at a first time at a start or prior to the injection of the bolus in order to derive the pressure in the infusion line at the first time, and measuring a second measurement value at a second time at an end of or after the injection of the bolus in order to derive the pressure in the infusion line at the second time, and the step of determining the control parameter comprising determining the control parameter according to an equation taking a difference in pressure between the first time and the second time, a volume of the bolus, and an expected slope during a pressure rise in case of an occluded infusion line into account, wherein a quotient of the difference in the pressure and the volume of the bolus corresponds to an actual slope.

12. An infusion device for administering a medical fluid to a patient, comprising:

a pumping mechanism for pumping a medical fluid through an infusion line towards a patient, a sensor device for measuring a measurement value indicative of a pressure in the infusion line, and a control device configured to control the pumping mechanism for injecting a bolus of the medical fluid into the infusion line, the control device being configured to determine, dependent on an injection of the bolus into the infusion line, a control parameter taking a change in the pressure during the injection of the bolus into account and to derive, from the control parameter, a presence of an abnormal condition during the injection of the bolus, the sensor device being configured to measure a first measurement value at a first time at a start or prior to the injection of the bolus in order to derive the pressure in the infusion line at the first time, and to measure a second measurement value at a second time at an end of or after the injection of the bolus in order to derive the pressure in the infusion line at the second time, the control device being configured to determine the control parameter according to an equation taking the difference in pressure between the first time and the second time, a volume of the bolus, and an expected slope during a pressure rise in case of an occluded infusion line into account, and the control device being configured to determine the control parameter according to the equation $$C = \frac{P(t_2)[\text{bar}] - P(t_1)[\text{bar}]}{V_{Bolus}[\text{ml}] \cdot \text{Expected\_Slope}[\text{bar}/\text{ml}]}$$

wherein

C is the control parameter, $P(t_1)$ is the pressure in the infusion line at the first time and $P(t_2)$ is the pressure in the infusion line at the second time, $V_{Bolus}$ is the volume of the injected bolus, and Expected_Slope corresponds to the expected slope during a pressure rise in case of an occluded infusion line.

13. The infusion device according to claim 12, further comprising an input device configured to allow a user to request the bolus, the control device configured to control the pumping mechanism for injecting the bolus of the medical fluid into the infusion line upon a user's request input via the input device.

14. The infusion device according to claim 12, wherein the expected slope is determined taking a compliance of a syringe, a compliance of the infusion line, a stiffness of the pumping mechanism and/or a dimension of a cylindrical tube into account.

15. The infusion device according to claim 14, further comprising a storage device, wherein values for the compliance of the syringe, the compliance of the infusion line, the stiffness of the pumping mechanism and/or the dimension of the cylindrical tube are stored in the storage device of the infusion device for at least one syringe used on the infusion device.

16. The infusion device according to claim 12, wherein the control device is configured to conclude the presence of an abnormal condition during the injection of the bolus if the control parameter is larger than a first bound and/or is smaller than a second bound greater than the first bound.

17. The infusion device according to claim 16, wherein the first bound is 0.5, and/or the second bound is 1.5.

18. The infusion device according to claim 12, further comprising an output device for outputting an alarm message, wherein the control device is configured to trigger the output of an alarm message in case it is derived that an abnormal condition during the injection of the bolus is presented.

19. The infusion device according to claim 12, wherein the abnormal condition corresponds to a closed stopcock preventing flow through the infusion line.

20. The infusion device according to claim 12, wherein the infusion device is a syringe pump.

* * * * *